(12) United States Patent
Tevs et al.

(10) Patent No.: US 6,661,514 B1
(45) Date of Patent: Dec. 9, 2003

(54) TUBE BLOCKAGE MONITOR

(75) Inventors: Nikolai R. Tevs, Winnipeg (CA); Edwin M. Bethune, Winnipeg (CA); Rasvan N. Dragne, Winnipeg (CA)

(73) Assignee: Vansco Electronics Ltd., Winnipeg (CA)

( * ) Notice: Subject to any disclaimer, the term of this patent is extended or adjusted under 35 U.S.C. 154(b) by 0 days.

(21) Appl. No.: 09/505,839

(22) Filed: Feb. 17, 2000

(51) Int. Cl.[7] .................. G01N 21/47; H01J 40/14; G08B 21/18
(52) U.S. Cl. ............ 356/337; 356/338; 250/222.2; 340/608; 340/684
(58) Field of Search ................ 356/436, 437, 356/337, 338; 340/684, 674, 606, 608; 250/222.2

(56) References Cited

U.S. PATENT DOCUMENTS

| | | |
|---|---|---|
| 4,697,173 A | * 9/1987 | Stokes .............. 365/230.06 |
| 5,177,470 A | 1/1993 | Repas |
| 5,831,539 A | 11/1998 | Thomas et al. |
| 5,831,541 A | 11/1998 | Paulson et al. |
| 5,831,542 A | 11/1998 | Thomas et al. |
| 5,883,383 A | 3/1999 | Dragne |
| 5,923,262 A | 7/1999 | Fuss et al. |

* cited by examiner

*Primary Examiner*—Zandra V. Smith
(74) *Attorney, Agent, or Firm*—Adrian D. Battison; Michael R. Williams; Ryan W. Dupuis

(57) ABSTRACT

A blockage monitor for detecting a blockage in flow of particles includes a sensor body for mounting on a wall of the seed duct and defining a front face flush with the duct surface carrying both an LED light source for projecting light into the interior of the duct and a phototransistor arranged to produce an output signal proportional to the intensity of reflected light received which increases as a seed passes. A separate blockage module counts the output and uses an algorithm for comparing the count with a calibration count to determine whether there is a blockage of the duct. A power voltage is supplied to each sensor using two wires. A test of the sensor includes a pulse in the power voltage so as to generate a corresponding but delayed pulse in the light from the light source.

20 Claims, 5 Drawing Sheets

TUBE BLOCKAGE MONITOR

This invention relates to an apparatus for detecting a blockage in flow of particles through a duct, which is particularly but not exclusively designed and arranged for use with seeders or planters where the particles passing through the duct are seeds.

The apparatus can be used for both air seeders where the seeds are carried through the duct in an air stream or can also be used with planters or seed drills where the seeds are dropped by gravity through a feed tube. The term "particles" used herein is not intended to indicate any size of the elements passing through the duct.

BACKGROUND OF THE INVENTION

There have previously been proposed systems for counting the number of seeds flowing in a duct and generally such systems utilize optical sensors at the duct including a transmitter on one side of the duct and a receiver on the other side of the duct arranged so that substantially the whole of the duct is visible in the light zone between the two elements.

Various designs have been proposed in a number of prior art patents including for example U.S. Pat. No. 5,883,383 (Dragne) assigned to the present assignees. These devices are relatively complex and therefore carry a significant cost. The devices are primarily designed for counting seeds in a seed duct and some operators choose to avoid the complexity and cost of an accurate counting system and require only a system which indicates blockage of a tube.

Air seeders are particularly prone to blockages at the seed discharge duct and unless the blockage is detected, the seeder can continue operating for a considerable period of time while missing a whole row thus leading to a significant loss in production in the finished crop.

One example of a blockage monitor of this type is shown in U.S. Pat. No. 5,177,470 (Repas) assigned to the present assignees. This arrangement includes a pin sensor which projects through the wall of the duct into the interior of the duct so that some of the seeds passing through the duct impinge upon the pin causing generation of a pulse by a piezo-electrical crystal in the pin. This device has achieved significant commercial success but some concern has arisen due to the use of a projecting element which extends into the duct and therefore can itself interfere with the flow of seeds.

There is therefore a desire to replace the projecting pin with an alternative system for detecting the passage of seeds which avoids elements projecting into the interior of the duct.

U.S. Pat. No. 5,831,542 (Thomas et al) assigned to Deere and company discloses a flexible generally flat piezo electric seed sensor element inserted at an acute angle of about thirty degrees into the seed flow duct. This is intended to replace the projecting pin and thus reduce the impingement of the detection system into the duct itself. However, there is still some interference with the flow of seeds by the detection system so that this proposal does not wholly overcome the problem.

A further alternative arrangement utilises the same transmitter and receiver in the seeder system which is proposed for seed counting systems. This arrangement can operate effectively, as has been evidenced by the success of the seed counting system, but carries a significant additional cost in due of the complexity of the sensor element and the greater difficulty of communication with that sensor element. Such sensor elements generally require the use of a three wire transmission system to separate the power supply from the signal transmission to allow detection of the signal at the separate blockage module.

Further elements relevant to the above U. S. Pat. No. 5,831,542 are shown in U. S. Pat. Nos. 5,923,262, 5,831,541 and 5,831,539, all assigned to Deere and company.

SUMMARY OF THE INVENTION

It is one object of the present invention to provide an improved blockage monitor which allows a simple inexpensive construction without any impingement of the sensor into the duct.

According to a first aspect of the invention there is provided an apparatus for detecting a blockage in flow of particles through a duct comprising:

a sensor having a sensor body for mounting on a wall of the duct and a sensor face for presentation to the interior of the duct;

a light source mounted on the sensor body for projecting light from the light source through the sensor face into the interior of the duct;

a light receptor mounted on the sensor body at the sensor face adjacent the light source so as to be responsive to light projected into the interior of the duct and reflected from surfaces in the duct to produce an output signal proportional to the intensity of reflected light received such that the output signal varies as a particle passes the sensor face;

a monitoring circuit responsive to the output signal to generate therefrom an output including a series of pulses representative of the passage of any particles;

a blockage module for receiving the output and for determining from the output whether there is a blockage of the duct sufficient to interfere with the flow of particles and to generate a warning signal in the event that a blockage is detected.

Preferably the sensor body includes a raised portion defining the sensor face which is substantially flush with an inside surface of the duct such that the light source and the receptor do not interfere with flow of particles.

Preferably the monitoring circuit is in the sensor body, wherein the blockage module is spaced from the sensor body and wherein a power voltage is supplied to the sensor using two wires only and the output including the series of pulses is communicated along the same two wires.

Preferably the monitoring circuit includes a comparator circuit for detecting when a change in the output signal exceeds a predetermined threshold and a communication circuit operable by the comparator circuit to generate a current pulse transmitted along the two wires detectable by the blockage module.

Preferably the communication circuit includes a transistor switch operable for connecting a current across the two wires to generate a current pulse which can be detected at the blockage module.

Preferably the light source includes a time delay circuit by which the LED current is delayed relative to a variation of power voltage on the connecting wires.

Preferably the light source includes a power supply which receives a power voltage from the blockage module along the connecting wires, wherein the blockage module is arranged to effect a test of the sensor by communicating to the sensor a pulse in the power voltage so as to generate a corresponding but delayed pulse in the light from the light source and wherein the monitoring circuit produces a pulse so that it is detectable by the blockage module separately from the pulse in the power voltage.

Preferably the blockage module including a processor providing a counter for counting the number of pulses in a predetermined time period and providing an algorithm for determining from the counted number whether there is a blockage; wherein there is provided a ground speed indicator for providing a speed input indicative of a ground speed of movement of the duct across ground onto which the particles are to be applied; and wherein there is provided a communication system for communicating the speed input to the blockage module for modifying the algorithm in dependence upon the ground speed.

Preferably the processor is arranged such that the algorithm includes a comparison of the counted number with a calibration counted number determined during a calibration period at a first ground speed, wherein there is determined to be a blockage when the counted number is reduced relative to the calibration number by a predetermined ratio and wherein the ratio is changed in dependence upon a difference between the ground speed and the calibration ground speed.

Preferably there is provided a plurality of ducts and a plurality of respective sensors and wherein each sensor has associated with it its own calibration counted number.

Preferably there is provided an application rate indicator for providing an application rate indicative of an intended rate of application of the particles to the ground onto which the particles are to be applied and the communication system is arranged for communicating the application rate to the blockage module for modifying the algorithm in dependence upon a change in intended application rate.

According to a second aspect of the invention there is provided an apparatus for detecting a blockage in flow of particles through a duct comprising:

a sensor for mounting on a wall of the duct;

the sensor having a light source for projecting light from the light source into the interior of the duct;

the sensor having a light receptor arranged to produce an output signal proportional to the intensity of light received such that the output signal varies as a particle passes the sensor;

the sensor having a monitoring circuit responsive to the output signal to generate therefrom an output including a series of pulses representative of the passage of any particles;

a blockage module for receiving the output and for determining from the output whether there is a blockage of the duct sufficient to interfere with the flow of particles and to generate a warning signal in the event that a blockage is detected;

wherein the blockage module is spaced from the sensor and wherein a power voltage is supplied to the sensor using two wires only and the output including the series of pulses is communicated along the same two wires;

wherein the monitoring circuit includes a comparator circuit for detecting when a change in the output signal exceeds a predetermined threshold and a communication circuit operable by the comparator circuit to generate a current pulse transmitted along the two wires detectable by the blockage module;

wherein the light source includes a power supply which receives a power voltage from the blockage module along the connecting wires;

wherein the blockage module is arranged to effect a test of the sensor by communicating to the sensor a pulse in the power voltage;

wherein the sensor is arranged so as to generate a corresponding but delayed pulse in the light from the light source;

and wherein the monitoring circuit generates the current pulse from the delayed pulse in light such that the delayed current pulse is detectable by the blockage module separately from the pulse in the power voltage.

According to a third aspect of the invention there is provided an apparatus for detecting a blockage in flow of particles through a duct comprising:

a sensor for mounting on a wall of the duct;

the sensor having a receptor arranged to produce an output including a series of pulses representative of the passage of any particles;

a blockage module for receiving the output and for determining from the output whether there is a blockage of the duct sufficient to interfere with the flow of particles and to generate a warning signal in the event that a blockage is detected, the blockage module including a processor providing a counter for counting the number of pulses in a predetermined time period and providing an algorithm for determining from the counted number whether there is a blockage;

a ground speed indicator for providing a speed input indicative of a ground speed of movement of the duct across ground onto which the particles are to be applied;

and a communication system for communicating the speed input to the blockage module for modifying the algorithm in dependence upon the ground speed.

Preferably the processor is arranged such that the algorithm includes a comparison of the counted number with a calibration counted number determined during a calibration period at a first ground speed, there is determined to be a blockage when the counted number is reduced relative to the calibration number by a predetermined ratio and the ratio is changed in dependence upon a difference between the ground speed and the calibration ground speed.

Preferably there is provided a plurality of ducts and a plurality of respective sensors and wherein each sensor has associated with it its own calibration counted number.

Preferably there is provided an application rate indicator for providing an application rate indicative of an intended rate of application of the particles to the ground onto which the particles are to be applied and the communication system is arranged for communicating the application rate to the blockage module for modifying the algorithm in dependence upon a change in intended application rate.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Reference is made to prior U.S. Pat. No. 5,177,470 which discloses an arrangement on which the present invention is closely based and the disclosure of that patent is incorporated herein by reference.

Reference is also made to U.S. Pat. No. 5,864,781 (White) assigned to the present assignee which discloses a system of communication between the components of the apparatus and the disclosure of that patent is incorporated herein by reference.

Figure 1:
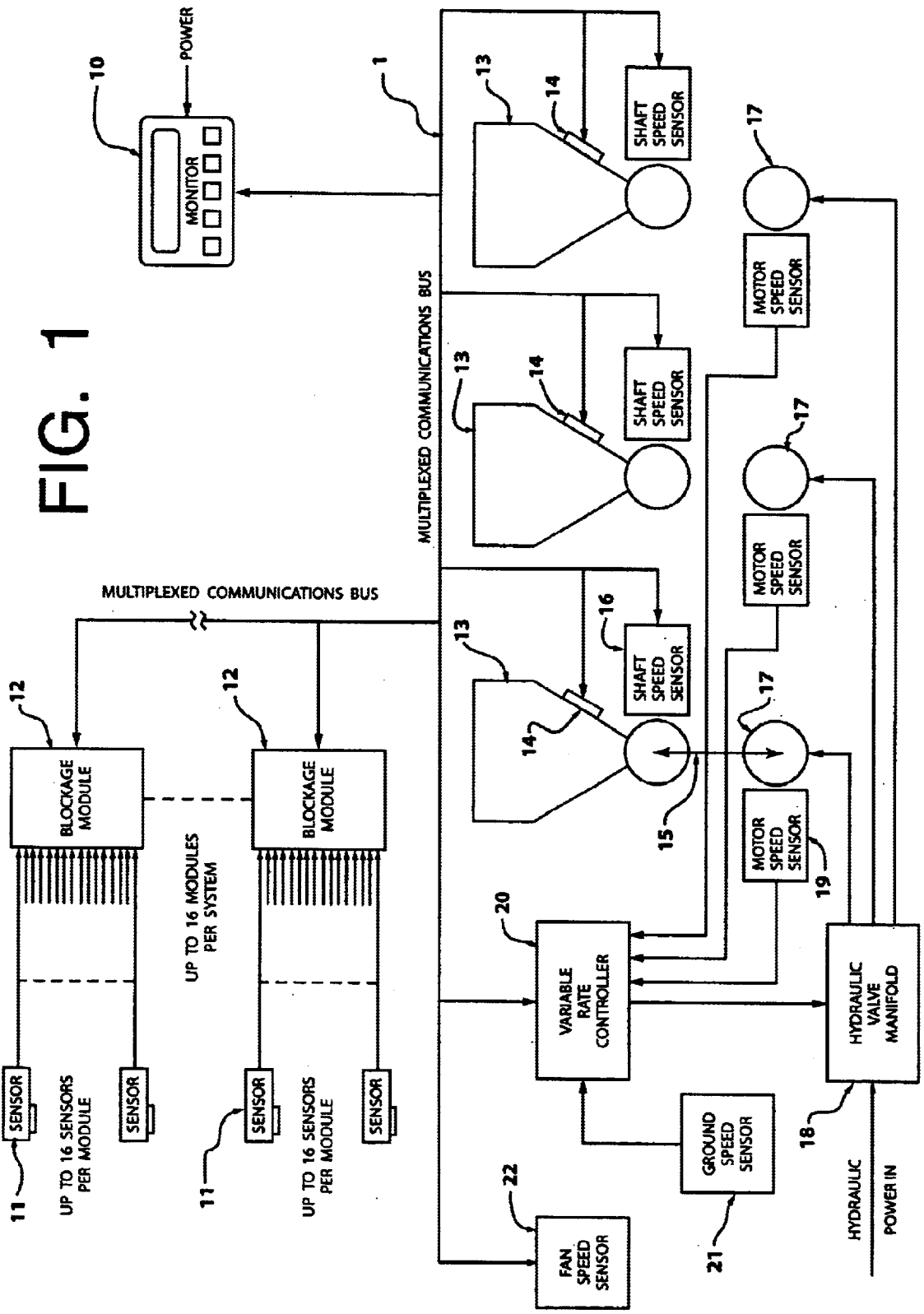
FIG. 1 is a block diagram of a monitoring and control system for a seeder, typically an air seeder, in which the control system can be used by an operator to control the rate of seeding.

Thus turning to the arrangement shown in FIG. 1, the apparatus comprises a monitor unit 10 housed within the tractor or control area for observation by the operator. The apparatus further includes a plurality of sensors 11, each of which is connected to a respective one of the ducts to the sensed. The sensors are connected to respective blockage modules 12. In the commercial embodiment of the present invention, there are up to 16 modules with each module having associated with it up to 16 sensors. However, these numbers can of course be modified in accordance with commercial requirements or an operating system may utilize only some of the sensor outlets of each of the blockage modules and may utilize only some of the blockage modules depending upon the total number of sensors required. The apparatus further comprises a priority of bins 13, each containing a material to be discharged over the ground. Each bin communicates through a series of ducts to individual seed discharge ducts which are arranged at the ground for discharging the seeds and other components from the bins 13 to the ground.

Each bin has a level sensor 14 which communicates with the communication bus 1 for communication to the monitor unit 10. Each bin is associated with a discharge arrangement including a drive shaft 15 which rotates at required speed to discharge the material at a required rate. The rate of rotation of he shaft 15 is detected by a shaft speed sensor 16 which again communicates to he bus 1. The shaft 15 is driven by a motor 17, the speed of which is controlled by valve system 18. The motor speed is sensed by a sensor 19 which feeds back information to a variable rate controller 20. Thus the variable rate controller receives information concerning the motor speed and effects control over the valve arrangement 18 for us to drive the motors 17 at the required speed.

The variable rate controller 20 can receive direct rate information from the monitor 10 on the bus 1 so that the operator can carry the rate manually by increasing or decreasing that rate for a selected period of time. The variable rate is also controlled by a ground speed sensor 21 which detects the ground speed of the apparatus and automatically therefore varies the application rate in dependence upon the ground speed to ensure that the rate per linear distance travelled remains unchanged despite changes in ground speed, unless that rate per linear distance is adjusted by the operator at the module 10.

Information from the ground speed sensor is also communicated to the bus 1 so that it can be fed back to the monitor 10. Information of the monitor 10 concerning the rate set at a predetermined time is also communicated on the bus 1 so that data relating to both of these elements is available on the bus 1.

The apparatus further includes a fan speed sensor 22 which detects speed of the drive fan for communication to the monitor 10. Other data can also be detected by various sensors and communicated to the monitor 10 or displayed to the operator if required.

The system for communication of data on the bus is disclosed in the above US patent of White assigned to the present assignee, the disclosure which is incorporated herein by reference.

Figure 2:
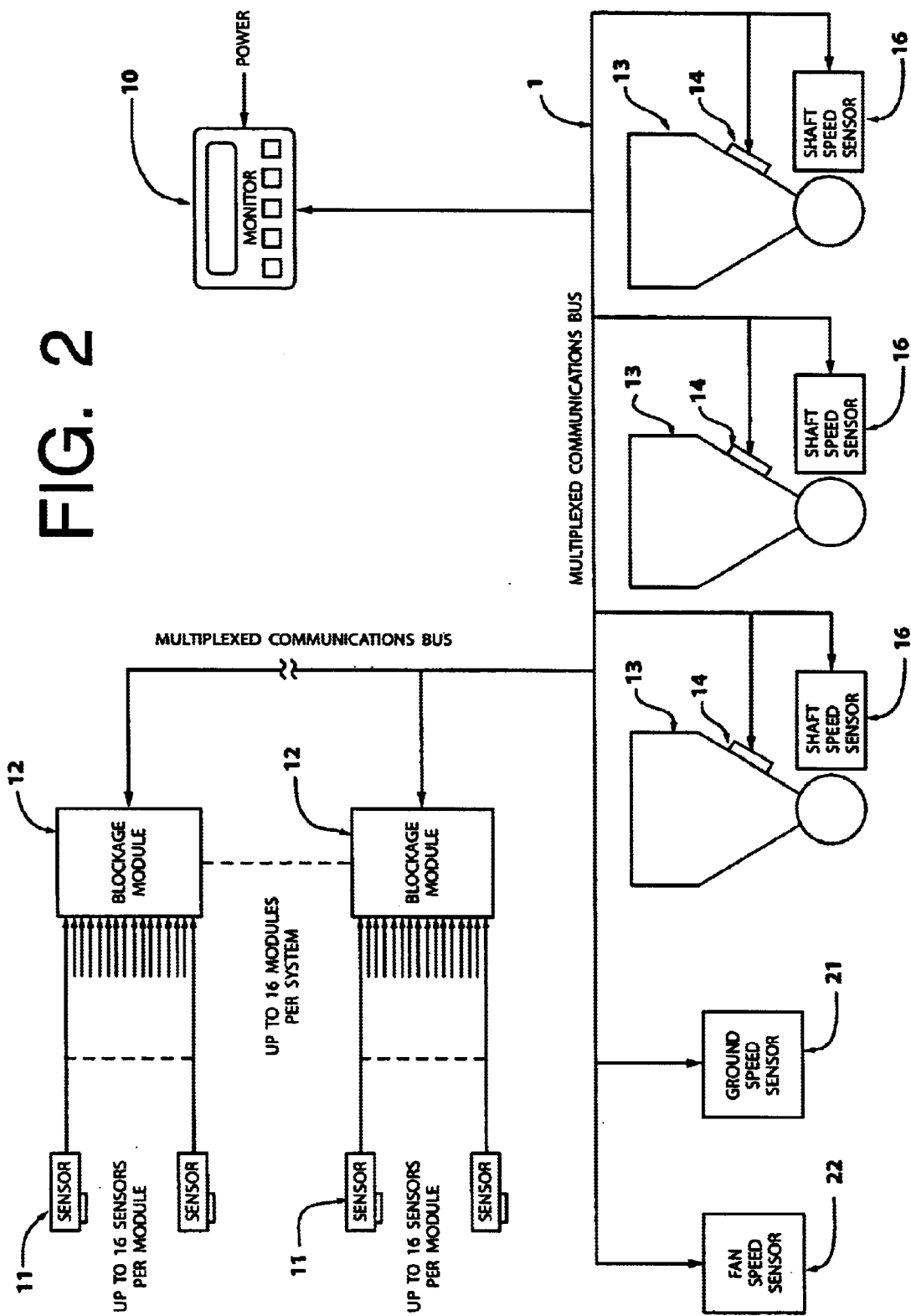
FIG. 2 is a block diagram similar to that of FIG. 1 which is simplified for monitoring only.

In FIG. 2 there is shown a simplified form of the apparatus of FIG. 1 in which there is no direct control of the application rate by the monitor 10 since the motors 17 and there associated control elements are omitted. In this case, the ground speed sensor communicates directly and only to the bus so that the information is available to the monitor 10 but there is no control of the application rate in dependence upon the ground speed and the application rate therefore remains unchanged.

The present invention is primarily concerned with the sensors 11 and their communication to and co-operation with the blockage modules 12.

Figure 5:
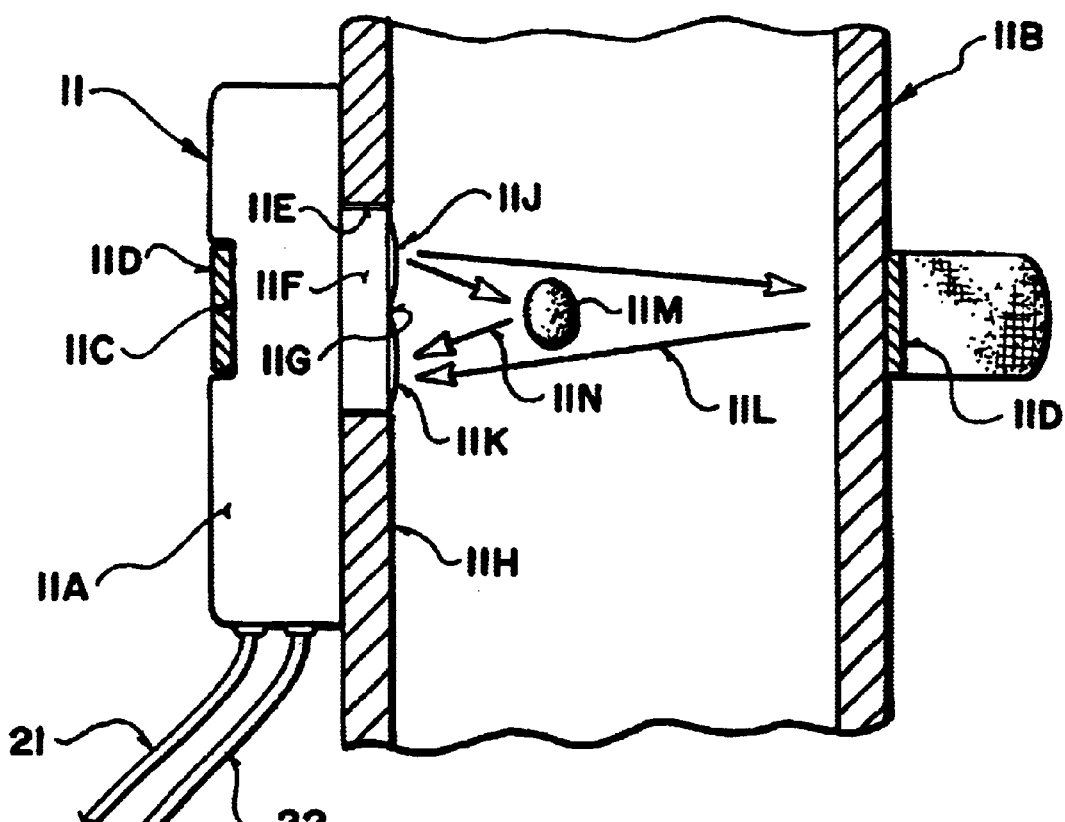
FIG. 5 is a longitudinal cross sectional view through one duct showing the physical construction of one sensor of FIG. 1 or 2.
Figure 6:
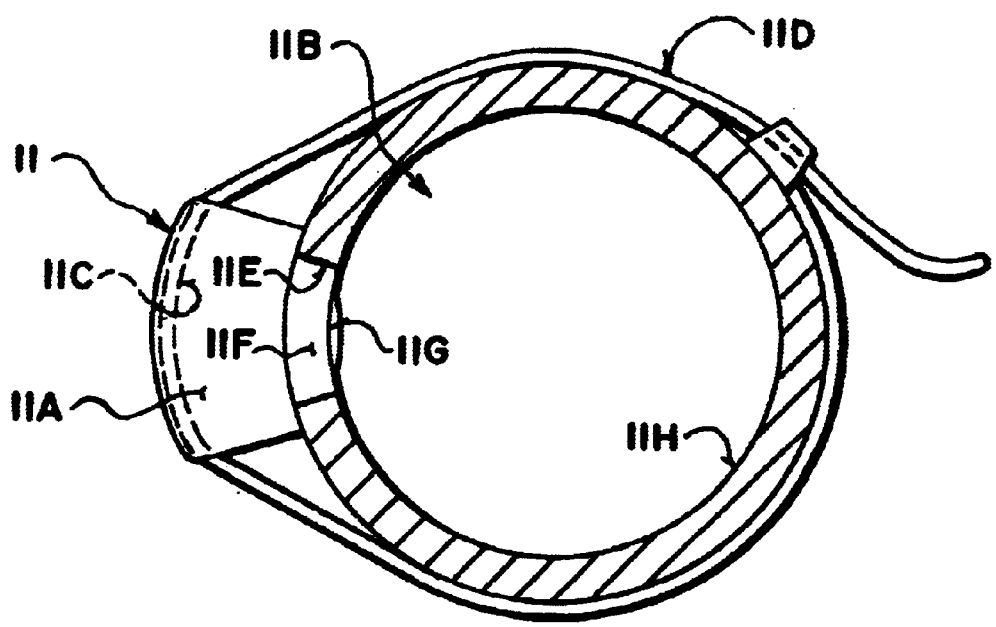
FIG. 6 is a transverse cross sectional view through one duct showing the physical construction of one sensor of FIG. 1 or 2.

In FIG. 5, is shown one of the sensors 11 which includes a sensor body 11A mounted on a duct 11B which is to be monitored. The sensor body 11A has a groove 11C by which it can be attached to the exterior of the duct at one side of the duct by a strap 11D. The duct has a circular hole 11E formed in the side wall at the one side adjacent the body 11A and a circular cylindrical projection 11F on the body projects into the hole 11E defining a circular front face 11G substantially flush with the inside surface 11H of the duct. The front face carries a light source 11J and a receptor 11K both of which are provided on the face 11G side by side. The light source and the receptor are substantially flush with the front face so again they do not interfere with or project into the interior of the duct.

The light source and the receptor are mounted on the front face so that they are adjacent but without direct line of sight communication between them so that the receptor receives light reflected from surfaces inside the duct. Thus the receptor 11K receives a level of reflected light as indicated schematically at 11L which is dependent upon the characteristics of the inside surface and is generally steady. In the presence of a seed 11M, light is reflected as schematically indicated at 11N and in view of the presence of the seed at a relatively close position to the surface 11G, the passage of a seed acts to increase momentarily the light in terms of the falling receptor 11K. Not all seeds are sufficiently close to effect an increase in intensity and therefore only some of the seeds are detected.

Figure 4:
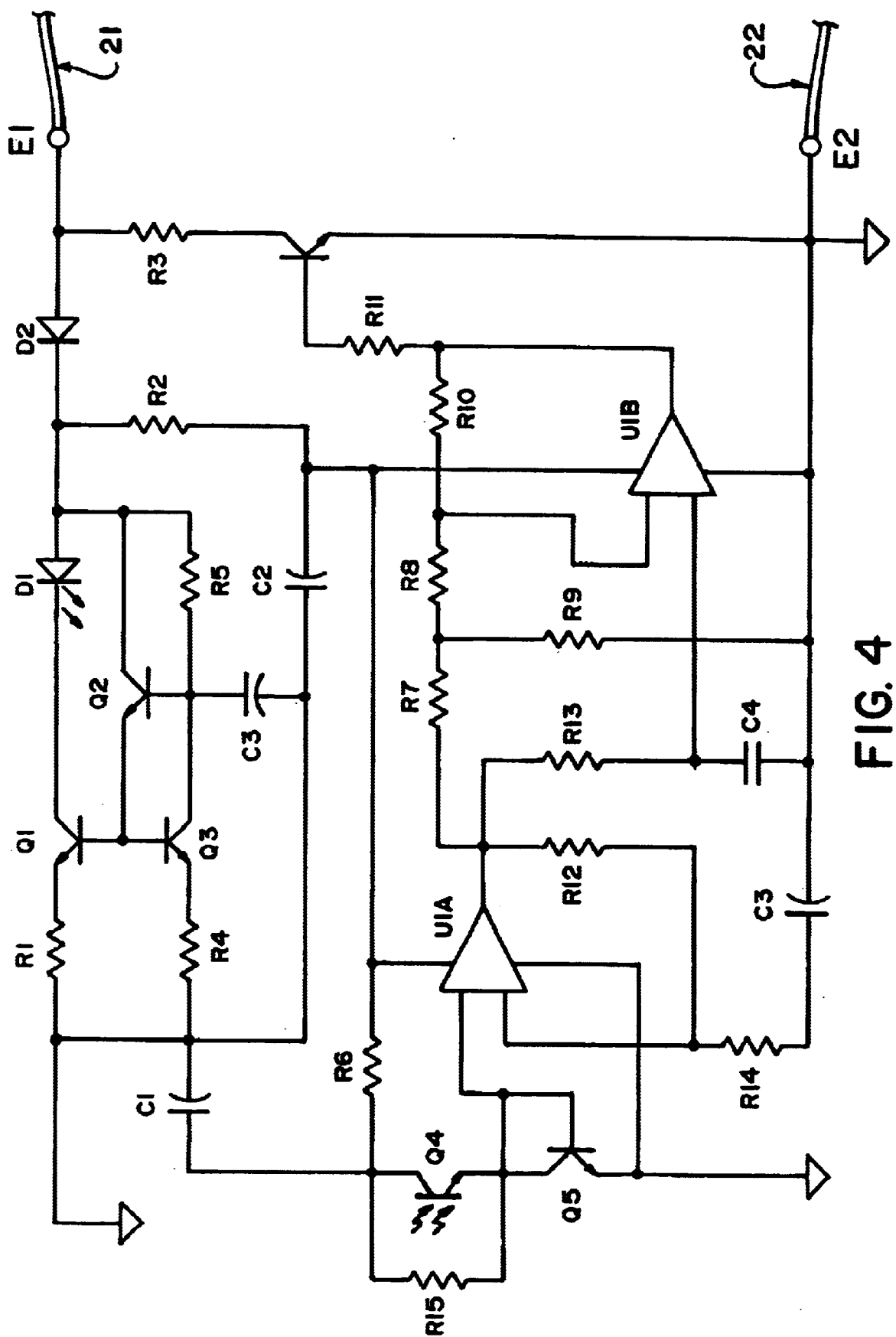
FIG. 4 is a circuit diagram showing the construction of one sensor of FIG. 1 or 2.

Turning now, to FIG. 4, the circuit components of sensor 11 are shown for connection to two wires 21 and 22 which transmit the power and data signals.

The transmitter 11G comprises LED D1. The light receiver or receptor comprises a photo transistor Q4.

The LED D1 is driven by an LED current source defined by transistors Q1, Q2 and Q3 together with resistors R1, R4 and R5 and capacitor C3. Resistor R5 and capacitor C3 form a time delay circuit and determine time delay between a variation of the power voltage and the variation of the emitted light. The current source thus generates a constant current across the LED D1 which is proportional to a voltage at terminal E1 connected to the positive supply line 21 of the wires 21 and 22. The wire 22 is connected to a terminal E2 at ground. The current source thus maintains, for a constant voltage supply at terminal E1, a constant output of light intensity from the LED D1. In the event that the voltage is reduced, the current is reduced proportionally and thus the light intensity is similarly reduced proportionally.

The light receiver photo transistor Q4, has an output current supplied to a logarithmic load defined by transistor Q5. The output from transistor Q5 is supplied as an input to AC-amplifier UA1 which is controlled by resistors R12 and R14 together with capacitor C5. The output from the amplifier is supplied to a comparator U1B which is controlled by resistors R7, R8, R9, Ri0 and R13 together with capacitor C4.

The output from the comparator is supplied to a communication circuit, defined by transistor Q6, the current from which is controlled by resistors R3 and R11. Resistor R15 is used to set a minimal offset current through the logarithmic load. Diode D2 is provided to protect the circuit against a reverse of the polarity of the power supply. A filter is provided by capacitors C1, C2 together with resistors R2 and R6 to decrease power supply ripple.

In the normal operation, the supply voltage (8volts) is applied to he terminal E1 from the blockage module. The current source provides a constant current (14 mA) through LED D1 that emits the constant intensity of infra red light into the duct.

Part of the reflected light from the LED D1 falls on the receiver transistor Q4 that converts the received light into a steady state constant current. This current flows through the logarithmic load and generates DC voltage on the non-inverted input of operational amplifier UA1. The same voltage appears on the amplifier output, on the capacitor C5 and on the inverting input of the comparator U1B. In a steady state, the input voltage on the non-inverting pin of the comparator U1B is lower than the voltage on the inverting pin and the output voltage is zero. The communication circuit defined by the output transistor Q6 is thus off.

In the presence of a particle, such as a seed, in the area of the duct that is close to the transmitter, additional light is reflected to the receiver as previously described and increases a voltage drop across the logarithmic load. This AC signal is amplified by the amplifier UA1 and triggers the comparator to generate an output signal supplied to the base of the output transistor Q6.

The output of the comparator opens transistor Q6 and causes current to flow across the terminals E1 and E2 thus creating a current pulse on the power supply line.

The blockage monitor described herein after acts to monitor the current flow on the power line supplied between the wires 21 and 22 and detects current pulses across the terminals E1 and E2 which represents the passage of seeds moving in front of the sensor.

The comparator is thus arranged with a predetermined threshold which ensures that noise does not act to trigger the output and only a sufficient changing intensity of the light generates a sufficient pulse at the comparator to change the state of the comparator and generate a current pulse at the output.

In general, therefore, the two wires that the blockage module supplies to each of the sensors act, to power the sensor and, in addition, allows the detection of pulses representing seeds to be communicated along the same two wires.

Figure 3:
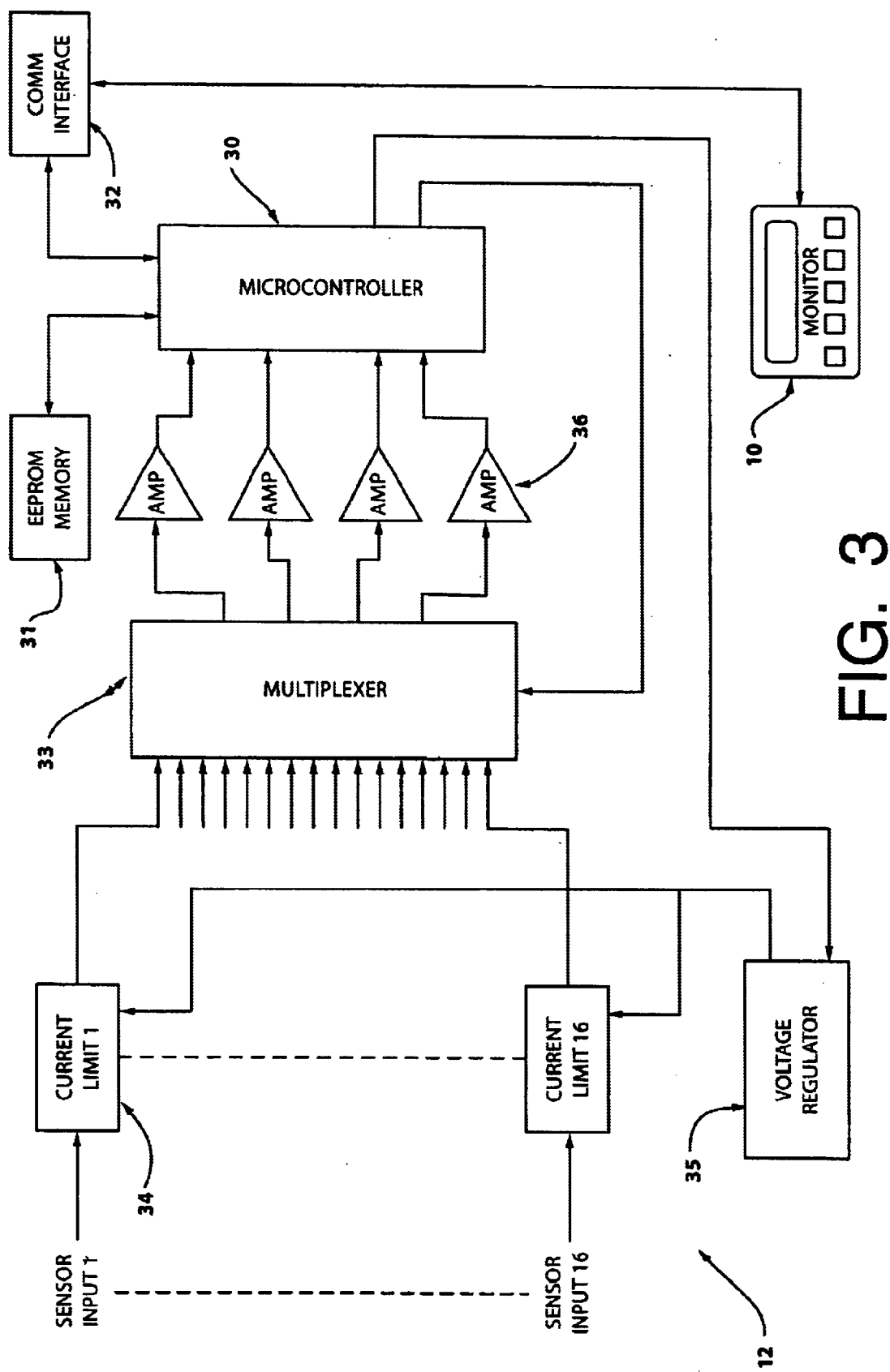
FIG. 3 is a block diagram showing the construction of one blockage module of FIG. 1 or 2.

As shown in FIG. 3, the blockage module 12 comprises a micro controller 30 having a memory unit 31 and a communication interface 32. The interface 32 acts to communicate data onto and to receive data from the communication bus 1.

The module further includes a multiplexer 33 which acts to communicate with the respective sensors 1–16. Each sensor is connected to a current limit device 34 which ensures that a short circuit does not cause damage to the module. A voltage regulator 35 acts to supply the required power voltage to each of the sensors through the current limit device 34 connected across the lines 21 and 22.

The multiplexer 33 is arranged to connect to four of the sensors simultaneously with the output of each sensor being supplied to a respective one of four amplifiers 36, each of which provides an input to the microcontroller 30. The multiplexer under the control of the microcontroller thus acts to look at the output from four sensors at a time and to cycle between the sensors four at a time repeatedly. The use of four input lines at the multiplexer ensures a faster response time since the sensors are monitored four times faster than they would be on a single multiplex system.

In general, the blockage module analyses the output from each of the sensors and detects the presence of a blockage at one or more of the sensors and if such a blockage should occur, acts to communicate that information to the monitor 10 to provide an alarm to the operator.

More specifically, the system undertakes the following steps.

1. Self Test:

An initial self test is effected either at power-up, or on operation of a self test button activated by the operator. The self test is effected by the microcontroller of each blockage module in turn effecting supply to the respective sensors of pulses in the voltage supply. Thus the supply voltage at the input terminals E1 and E2 is reduced by a predetermined voltage pulse for predetermined time, with that voltage pulse, through the current source and delay circuit, acting to generate a corresponding but delayed reduction in light intensity at the transmitter D1.

In the event that the sensor is functional and is sufficiently clean to allow proper detection to occur, a corresponding delayed pulse will be transmitted to the receiver Q4. In the event that the sensor is defective or is dirty to an extent sufficient to prevent proper light communication between the transmitter and receiver, no such pulse of a required magnitude is detected.

As previously described, the delay in the generation of the current pulse by the light source causes the current pulse at the output transistor Q6 to be delayed relative to the voltage pulse by a sufficient time that the current pulse is moved to a location relative to the voltage pulse that it can be detected separately from the voltage pulse. This is achieved by selecting the time period of the voltage relative to the delay time period.

The simple circuit arrangement therefore utilising the same two wires to communicate the power and to communicate the output signals allows the generation of pulses at the output which can be determined by the blockage module to ensure that the light transmitter and receiver are operating within acceptable limits.

The multiplexer scans through the sensors as previously explained and the pulse is communicated to the microcontroller for each sensor in turn providing indication that the sensor is operative and operating within acceptable limits. In the event that any such sensor is determined to be defective or outside the limits, the microcontroller determines this status and communicates the status through the communication interface to the bus and therefore to the central monitor. In the event that that operator is informed of a defective sensor, the operator will normally service the sensor by replacement or cleaning so that the self test can be repeated to ensure that all sensors are operating effectively.

2. Calibration:

In the event that the self test is completed satisfactorily the system next goes to a calibration process similar to that disclosed in the above US patent of Repas. The calibration system acts for each separate sensor to monitor that sensor for a pre-determined period of time and to record in the respective microcontroller for that sensor a number which is representative of the number of pulses detected in the pre-determined time period. The calibration is effected at a predetermined and pre-set ground speed and application rate as determined by the operator. Thus the operator moves the equipment at the required ground speed and inputs into the monitor the required application rate so that this is effected by the control system as previously explained.

Therefore during the normal operation that the required application rate and the required ground speed, the calibration system generates a number which is representative of the number of pulses in a predetermined time period. As explained in the previous patent, the time period can be varied in the event that a pre-selected number of pulses is not received to ensure that the system is operating within suitable parameters. The number of pulses can thus be of the order of 25–50 since this number allows detection within a relatively small time period but provides a large enough number for a statistical analysis to determine whether blockage is present.

Thus each sensor has associated with it a calibration number stored in the microcontroller. When calibration has successfully occurred, a signal is supplied to the central monitor to inform the operator that calibration is complete. The monitor will continuously display the sensors that are not yet calibrated. If one or more sensors fails to calibrate, those will be displayed on the monitor. The ones that have been calibrated will not be displayed. The operator can investigate the problem and take whatever action is necessary. If the sensor has passed the selftest, the problem is likely not with the sensor. There is no predetermined time limit to declare calibration failure. The operator will see that the other sensors are calibrated and that one or more remain. It is up to the operator to make the judgement that a reasonable time for calibration has elapsed and to take the necessary action suitable in the circumstances.

Calibration is determined to have failed in the event that a predetermined number of pulses cannot be obtained within a predetermined time limit.

The use of different calibration numbers for each of the sensors ensures that the sensors can be used in different situations and in different operating locations in the system where the number of seeds passing may be significantly different from that at other locations. Each sensor therefore is independent and its responsive to its own conditions rather than to those of other sensors.

3. Monitoring Operation:

After calibration is successfully completed, the system automatically enters the monitoring mode and repeatedly acts to monitor each sensor in turn using the multiplex system as previously described to detect the number of pulses within a predetermined time period and to compare that number with the calibration number previously stored.

In the event that the detected number is less than the calibration number by a predetermined ratio, the microcontroller is programmed to generate a flag for that sensor indicative of a blockage. The ratio can be determined empirically and can be varied in accordance with operating conditions or various other characteristics of the system.

In the event that the ground speed, as detected by the ground speed sensor changes, the algorithm by which the controller detects the presence of a blockage is modified so as to multiply the detected number by the ratio of current ground speed relative to original pre-set ground speed and then to compare the calculated number with the calibration number based upon the above stated difference ratio. Thus the system takes into account variations in ground speed and uses this ratio of current ground speed to original ground speed in the algorithm in the calculation of a blocked condition.

In the arrangement of FIG. 1 where the application rate can be adjusted as input by the central monitor, the same arrangement is provided in which the ratio of current application rate to original application rate is applied to the counted number prior to its comparison with the calibration number. Again therefore, the system can automatically accommodate for changing an application rate as supplied as data on the bus 1 from the central monitor.

The system of FIG. 2 which does not allow a variation of the application rate does not and cannot provide automatic calculation for changes in application rate. However, the system of FIG. 2 also supplies the ground speed as data accessible to the blockage module and thus the ground speed is used in the algorithm for calculating presence of the blockage.

In the event that a blockage is indicated to the operator at the central monitor, the operator will normally halt operation to remove the blockage by a physically cleaning the system or other action which may be necessary.

When the equipment is restarted, the system continues to monitor the sensors based upon the original calibration numbers and recalculates an unblocked condition as a ratio of a current counted number to the calibration number. The ratio of the current counted number to the calibration number to reset that status of that sensor to an unblocked condition is different from that to initially set the status at a blocked condition. This provides hysteresis to ensure that the system does not oscillate between blocked and unblocked settings unless there is a significant change in the count number due to significant change in the condition in the duct.

The apparatus therefore provides a simple, inexpensive construction which can rapidly and accurately determine blockages while using a sensor which avoids impinging into the duct. The arrangement allows a simple two wire communication between the sensor and the module thus reducing cost.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

We claim:

1. Apparatus for detecting a blockage in flow of particles through a duct comprising:

a sensor for mounting on a wall of the duct;

the sensor having a receptor arranged to produce an output including a series of pulses representative of the passage of any particles;

a blockage module for receiving the output and for determining from the output whether there is a blockage of the duct sufficient to interfere with the flow of particles and to generate a warning signal in the event that a blockage is detected;

the blockage module including a processor providing a counter for counting the number of pulses in a predetermined time period and the processor containing algorithmic elements using which it can be determined from the counted number whether there is a blockage;

an application rate indicator for providing an application rate indicative of an intended rate of application of the particles to the ground onto which the particles are to be applied;

and a communication system arranged for communicating the application rate to the processor of the blockage module;

the processor being arranged to modify the algorithmic elements in response to a change in intended application rate received from the communications system;

wherein there is provided a monitoring circuit at the sensor;

wherein the blockage module is spaced from the sensor;

and wherein a power voltage is supplied to the sensor using two wires only and he output including the series of pulses is communicate along the same two wires.

2. The apparatus according to claim 1 wherein the sensor includes sensor body for mounting on a wall of the duct and a sensor face for presentation to an interior of the duct, a light source mounted on the sensor body for projecting light from the light source through the sensor face into the interior of the duct, a light receptor mounted on the sensor body at the sensor face adjacent the light source so as to be responsive to light projected into the interior of the duct and reflected from surfaces in the duct to produce an output signal proportional to the intensity of reflected light received such that the output signal varies as a particle passes the sensor face and a monitoring circuit responsive to the output signal to generate therefrom an output including a series of pulses representative of the passage of any particles.

3. The apparatus according to claim 2 wherein the sensor body includes a raised portion defining the sensor face which is substantially flush with an inside surface of the duct such that the light source and the receptor do not interfere with flow of particles.

4. The apparatus according to claim 1 wherein the monitoring circuit includes a comparator circuit for detecting when a change in the output signal exceeds a predetermined threshold and a communication circuit operable by the comparator circuit to generate a current pulse transmitted along the two wires detectable by the blockage module.

5. The apparatus according to claim 4 wherein the communication circuit includes a transistor switch operable for connecting a current across the two wires.

6. Apparatus for detecting a blockage in flow of particles through a duct comprising:

a sensor for mounting on a wall of the duct;

the sensor having a light source for projecting light from the light source into the interior of the duct;

the sensor having a light receptor arranged to produce an output signal proportional to the intensity of light received such that the output signal varies as a particle passes the sensor;

the sensor having a monitoring circuit responsive to the output signal to generate therefrom an output including a series of pulses representative of the passage of any particles;

a blockage module for receiving the output and for determining from the output whether there is a blockage of the duct sufficient to interfere with the flow of particles and to generate a warning signal in the event that a blockage is detected;

wherein the blockage module is spaced from the sensor and wherein a power voltage is supplied to the sensor using two wires only and the output including the series of pulses is communicated along the same two wires;

wherein the monitoring circuit includes a comparator circuit for detecting when a change in the output signal exceeds a predetermined threshold and a communication circuit operable by the comparator circuit to generate a current pulse transmitted along the two wires detectable by the blockage module;

wherein the light source includes a power supply which receives a power voltage from the blockage module along the connecting wires;

wherein the blockage module is arranged to effect a test of the sensor by communicating to the sensor a pulse in the power voltage;

wherein the sensor is arranged so as to generate a corresponding but delayed pulse in the light from the light source;

and wherein the monitoring generates the corresponding delayed current pulse such that the current pulse is detectable by the blockage module separately from the pulse in the power voltage.

7. The apparatus according to claim 6 wherein the comparator circuit includes a logarithmic load, an operational amplifier and a comparator.

8. The apparatus according to claim 6 wherein the sensor includes sensor body for mounting on a wall of the duct and a sensor face for presentation to an interior of the duct, the light source being mounted on the sensor body for projecting light from the light source through the sensor face into the interior of the duct, and a light receptor mounted on the sensor body at the sensor face adjacent the light source so as to be responsive to light projected into the interior of the duct and reflected from surfaces in the duct to produce an output signal proportional to the intensity of reflected light received such that the output signal varies as a particle passes the sensor face.

9. The apparatus according to claim 8 wherein the sensor body includes a raised portion defining the sensor face which is substantially flush with an inside surface of the duct such that the light source and the receptor do not interfere with flow of particles.

10. Apparatus for detecting a blockage in flow of particles through a duct comprising:

a sensor for mounting on a wall of the duct;

the sensor having a receptor arranged to produce an output including a series of pulses representative of the passage of any particles;

a blockage module for receiving the output and for determining from the output whether there is a blockage of the duct sufficient to interfere with the flow of particles and to generate a warning signal in the event that a blockage is detected;

the blockage module including a processor providing a counter for counting the number of pulses in a predetermined time period and the processor containing algorithmic elements using which it can be determined from the counted number whether there is a blockage;

a ground speed indicator for providing a speed input indicative of a ground speed of movement of the duct across ground onto which the particles are to be applied;

and a communication system for communicating the speed input to the processor of the blockage module;

the processor being arranged to modify the algorithmic elements in response to a change in the ground speed input received from the communication system;

wherein there is provided a monitoring circuit at the sensor;

wherein the blockage module is spaced from the sensor;

and wherein a power voltage is supplied to the sensor using two wires only and the output including the series of pulses is communicated along the same two wires.

11. The apparatus according to claim 10 wherein the processor is arranged such that the algorithmic elements include a comparison of the counted number with a calibration counted number determined during a calibration period at a first ground speed, wherein there is determined to be a blockage when the counted number is reduced relative to the calibration number by a predetermined ratio and wherein the ratio is changed in dependence upon a difference between the ground speed and the calibration ground speed.

12. The apparatus according to claim 11 wherein there is provided a plurality of ducts and a plurality of respective sensors and wherein each sensor has associated with it its own calibration counted number.

13. The apparatus according to claim 12 wherein there is provided an application rate indicator for providing an application rate indicative of an intended rate of application of the particles to the ground onto which the particles are to be applied and wherein the communication system is arranged for communicating the application rate to the blockage module for modifying the algorithm in dependence upon a change in intended application rate.

14. The apparatus according to claim 10 wherein the sensor includes sensor body for mounting on a wall of the duct and a sensor face for presentation to an interior of the duct, a light source mounted on the sensor body for projecting light from the light source through the sensor face into the interior of the duct, a light receptor mounted on the sensor body at the sensor face adjacent the light source so as to be responsive to light projected into the interior of the duct and reflected from surfaces in the duct to produce an output signal proportional to the intensity of reflected light received such that the output signal varies as a particle passes the sensor face and a monitoring circuit responsive to the output signal to generate therefrom an output including a series of pulses representative of the passage of any particles.

15. The apparatus according to claim 14 wherein the sensor body includes a raised portion defining the sensor face which is substantially flush with an inside surface of the duct such that the light source and the receptor do not interfere with flow of particles.

16. The apparatus according to claim 10 wherein the monitoring circuit includes a comparator circuit for detecting when a change in the output signal exceeds a predetermined threshold and a communication circuit operable by the comparator circuit to generate a current pulse transmitted along the two wires detectable by the blockage module.

17. The apparatus according to claim 16 wherein the communication circuit includes a transistor switch operable for connecting a current across the two wires.

18. Apparatus for detecting a blockage in flow of particles through a duct comprising:

a sensor for mounting on a wall of the duct;

the sensor having a receptor arranged to produce an output including a series of pulses representative of the passage of any particles;

a blockage module for receiving the output and for determining from the output whether there is a blockage of the duct sufficient to interfere with the flow of particles and to generate a warning signal in the event that a blockage is detected;

the blockage module including a processor providing a counter for counting the number of pulses in a predetermined time period and the processor containing algorithmic elements using which it can be determined from the counted number whether there is a blockage;

an application rate indicator for providing an application rate indicative of an intended rate of application of the particles to the ground onto which the particles are to be applied;

and a communication system arranged for communicating the application rate to the processor of the blockage module;

the processor being arranged to modify the algorithmic elements in response to a change in intended application rate received from the communications system;

wherein there is provided a ground speed indicator for providing a speed input indicative of a ground speed of movement of the duct across ground onto which the particles are to be applied and a communication system for communicating the speed input to the processor of the blockage module, and wherein the processor is arranged to modify the algorithmic elements in response to the ground speed input received from the communication system.

19. The apparatus according to claim 18 wherein the processor is arranged such that the algorithmic elements include a comparison of the counted number with a calibration counted number determined during a calibration period at a first ground speed, wherein there is determined to be a blockage when the counted number is reduced relative to the calibration number by a predetermined ratio and wherein the ratio is changed in dependence upon a difference between the ground speed and the calibration ground speed.

20. The apparatus according to claim 19 wherein there is provided a plurality of ducts and a plurality of respective sensors and wherein each sensor has associated with it its own calibration counted number.

* * * * *